(12) United States Patent
Kanno et al.

(10) Patent No.: US 8,617,055 B2
(45) Date of Patent: Dec. 31, 2013

(54) ENDOSCOPE APARATUS WITH PRIORITY-BASED DRIVING CONTROL ON IDENTIFIABLE PLURAL CONNECTIONS

(71) Applicant: Olympus Medical Systems Corp., Tokyo (JP)

(72) Inventors: Kiyotaka Kanno, Higashimurayama (JP); Koichiro Tabuchi, Tokyo (JP); Keisuke Tsutsui, Hino (JP); Makoto Ono, Sagamihara (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/651,812

(22) Filed: Oct. 15, 2012

(65) Prior Publication Data
US 2013/0150668 A1   Jun. 13, 2013

Related U.S. Application Data

(63) Continuation of application No. PCT/JP2011/065213, filed on Jul. 1, 2011.

(30) Foreign Application Priority Data

Jul. 7, 2010   (JP) .................. 2010-155193

(51) Int. Cl.
*A61B 1/00* (2006.01)
*A61B 1/04* (2006.01)

(52) U.S. Cl.
CPC ......... *A61B 1/00006* (2013.01); *A61B 1/00059* (2013.01); *A61B 1/00025* (2013.01); *A61B 1/00032* (2013.01)
USPC ............................. 600/118; 600/109; 600/132

(58) Field of Classification Search
CPC .......... A61B 1/00006; A61B 1/00059; A61B 1/00025; A61B 1/00027; A61B 1/00032
USPC .................................. 600/112, 118, 132, 109
See application file for complete search history.

(56) References Cited

U.S. PATENT DOCUMENTS

| 5,390,662 | A | 2/1995 | Okada |
| 2003/0199793 | A1* | 10/2003 | Sakurai et al. ..................... 601/2 |
| 2004/0019347 | A1* | 1/2004 | Sakurai et al. .................. 606/27 |
| 2007/0088193 | A1* | 4/2007 | Omori et al. .................. 600/101 |

(Continued)

FOREIGN PATENT DOCUMENTS

| EP | 2 090 216 A1 | 8/2009 |
| JP | 05-245104 | 9/1993 |

(Continued)

*Primary Examiner* — John P Leubecker
*Assistant Examiner* — Arnaldo Torres Diaz
(74) *Attorney, Agent, or Firm* — Scully, Scott, Murphy & Presser, P.C.

(57) ABSTRACT

An endoscope apparatus includes: a plurality of connection portions to which an endoscope can be connected, respectively, wherein a priority setting portion sets a connection priority of the plurality of connection portions, a drive portion supplies a drive signal to one endoscope and a control portion that controls so that the drive portion supplies the drive signal to any one endoscope only based on the connection priority. The endoscope apparatus further includes an identification portion that identifies the kind of endoscope based on a resistance value of a specific resistance that differs according to a kind of the endoscope that is arranged in the endoscope, and that is detected by cancelling a contact resistance in the connection portion.

4 Claims, 9 Drawing Sheets

(56) References Cited

U.S. PATENT DOCUMENTS

| | | | |
|---|---|---|---|
| 2007/0260233 A1* | 11/2007 | Miura | 606/27 |
| 2008/0091065 A1 | 4/2008 | Oshima et al. | |
| 2009/0105540 A1* | 4/2009 | Kawata et al. | 600/118 |
| 2009/0131929 A1* | 5/2009 | Shimizu | 606/34 |
| 2009/0209811 A1 | 8/2009 | Higuchi | |
| 2009/0228623 A1* | 9/2009 | Tsuchiya | 710/72 |
| 2010/0191121 A1* | 7/2010 | Satoh et al. | 600/459 |

FOREIGN PATENT DOCUMENTS

| | | |
|---|---|---|
| JP | 2008-086665 | 4/2008 |
| JP | 2009-095466 | 5/2009 |
| JP | 2009-189528 | 8/2009 |

* cited by examiner

ENDOSCOPE APARATUS WITH PRIORITY-BASED DRIVING CONTROL ON IDENTIFIABLE PLURAL CONNECTIONS

CROSS REFERENCE TO RELATED APPLICATION

This application is a continuation application of PCT/JP2011/065213 filed on Jul. 1, 2011 and claims benefit of Japanese Application No. 2010-155193 filed in Japan on Jul. 7, 2010, the entire contents of which are incorporated herein by this reference.

BACKGROUND OF INVENTION

1. Field of the Invention

The present invention relates to an endoscope apparatus to which a plurality of endoscopes can be connected.

2. Description of the Related Art

Endoscope systems that include an endoscope and an endoscope apparatus are widely used in a medical field and an industrial field and the like. For example, in the medical field, endoscope systems are used for observing living tissue and the like and for various kinds of treatment.

An endoscope apparatus to which two endoscopes of different kinds can be connected is disclosed in Japanese Patent Application Laid-Open Publication No. 2009-95466.

SUMMARY OF THE INVENTION

An endoscope apparatus of an embodiment of the present invention includes: a plurality of connection portions to which an endoscope can be connected, respectively; a priority setting portion that, when a plurality of endoscopes are connected to the plurality of connection portions, sets a drive priority for selecting one endoscope to supply a drive signal to; a drive portion that supplies a drive signal to one endoscope; and a drive control portion that controls so that the drive portion supplies the drive signal only to any one endoscope based on the drive priority.

DETAILED DESCRIPTION OF THE PREFERRED EMBODIMENT(S)

First Embodiment

Figure 1:
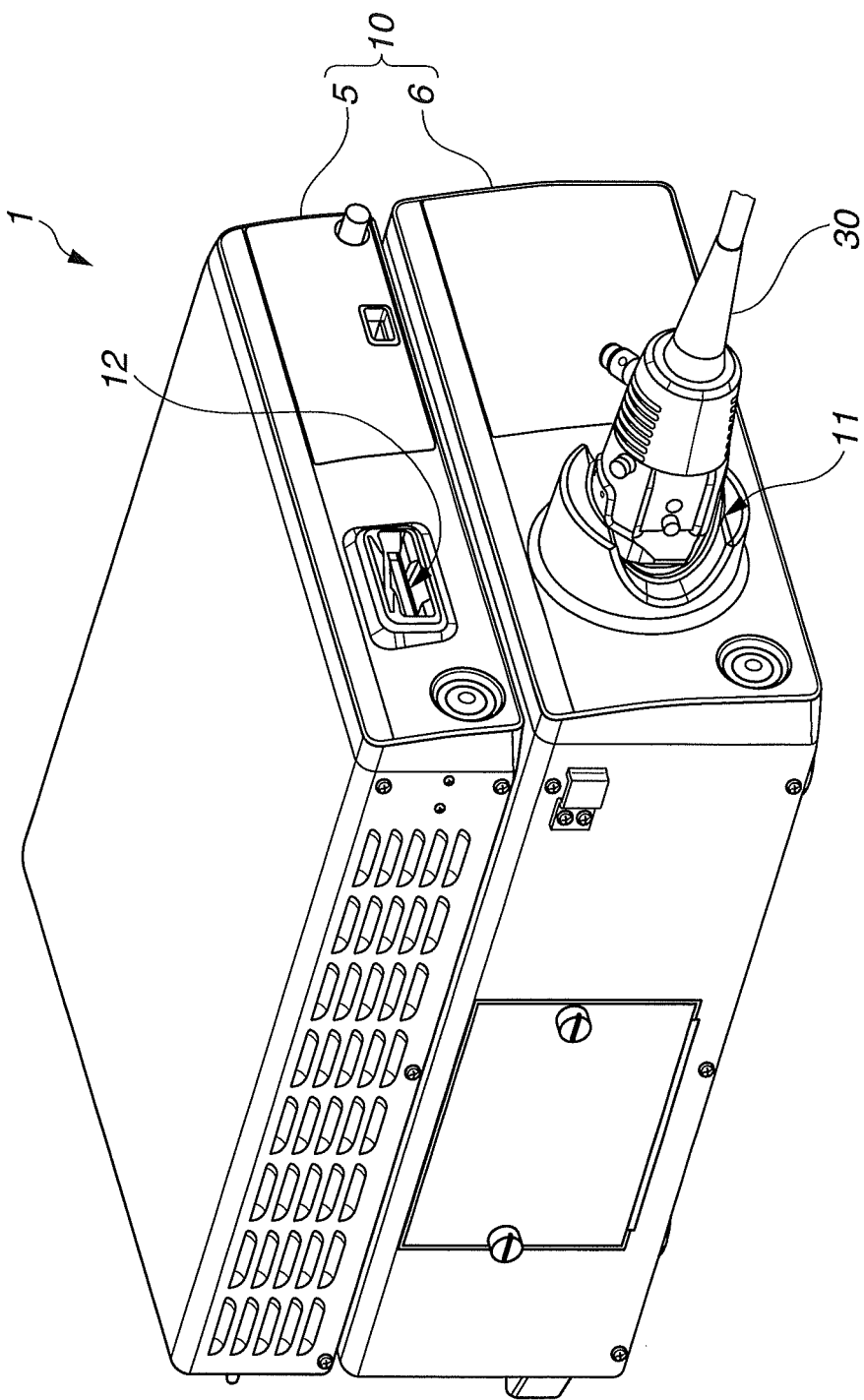
FIG. 1 is an overview diagram of an endoscope apparatus according to a first embodiment.

As shown in FIG. 1, an endoscope apparatus 10 according to a first embodiment of the present invention includes a light source apparatus 6 having a first connection portion 11 that is first connection means to which a first endoscope 30 is connectable, and a processor 5 having a second connection portion 12 that is second connection means to which a second endoscope 40 is connectable. Note that, in FIG. 1, an endoscope system 1 in a state in which the first endoscope (hereunder, also referred to as "scope") 30 is connected to the first connection portion 11, and an endoscope is not connected to the second connection portion 12 is illustrated.

Figure 2:
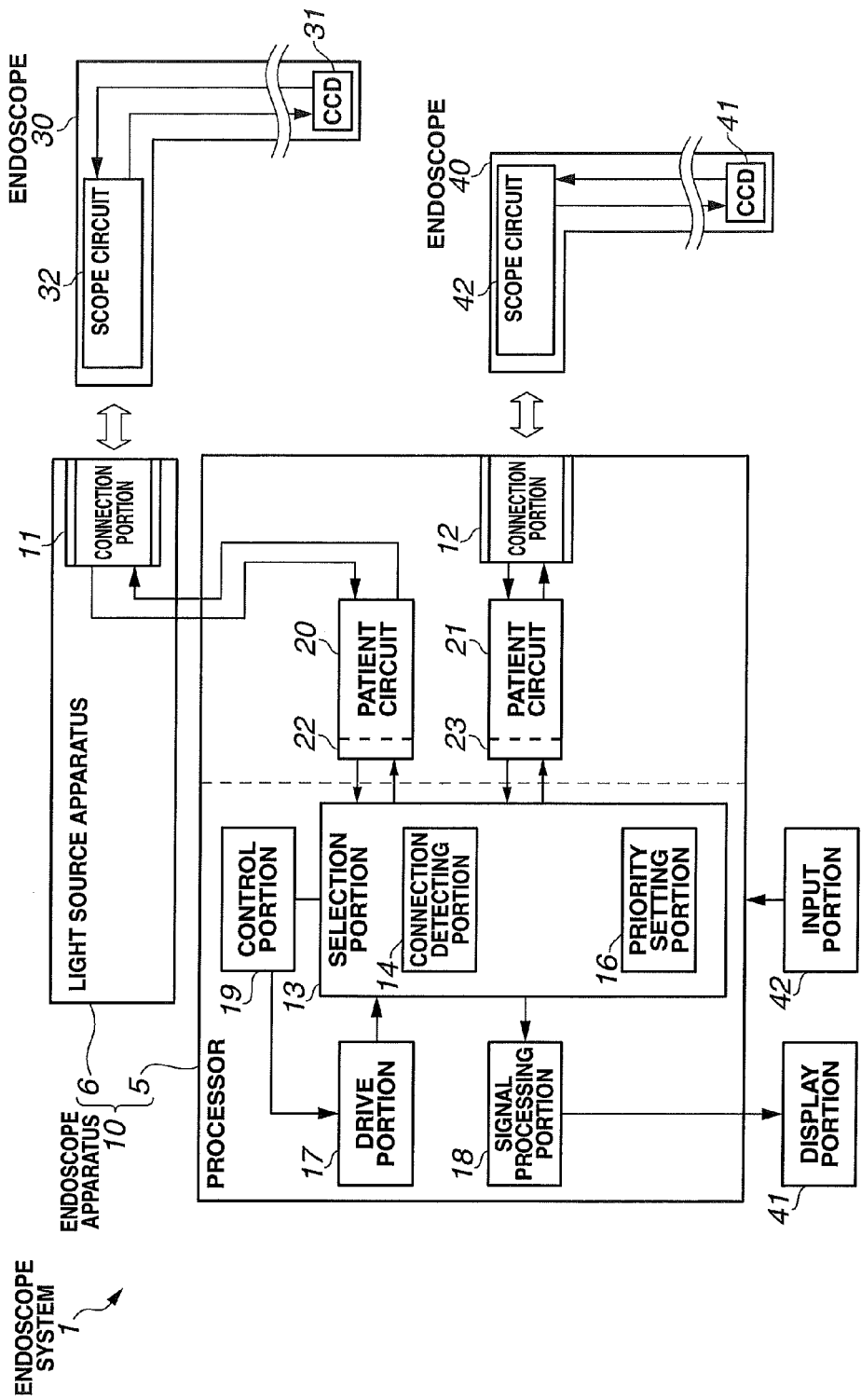
FIG. 2 is a configuration diagram of an endoscope system having the endoscope apparatus according to the first embodiment.

That is, the endoscope system 1 that is shown in FIG. 2 includes, for example, the first endoscope 30, the second endoscope 40, and the endoscope apparatus 10. The light source apparatus 6 includes a light source (not shown) such as a xenon lamp, and emits illuminating light from a distal end portion of a connected endoscope through a light guide (not shown) of the endoscope.

For example, the first endoscope 30 is a digital endoscope that converts an image pickup signal that is picked up by a CCD 31 that is an image pickup portion arranged at a distal end portion thereof into a digital signal in a scope circuit 32, and transmits the digital signal to the endoscope apparatus 10. In contrast, for example, the second endoscope 40 is an analog endoscope that transmits an image pickup signal that is picked up by a CCD 41 that is an image pickup portion arranged at a distal end portion thereof to the endoscope apparatus 10 as an analog signal.

As shown in FIG. 2, an image pickup signal of the first endoscope 30 that is connected to the light source apparatus 6 of the endoscope apparatus 10 is also subjected to signal processing in the processor 5, similarly to an image pickup signal of the second endoscope 40 that is connected directly to the processor 5. That is, in the endoscope apparatus 10, although the first endoscope 30 is connected to the light source apparatus 6, even when the two endoscopes 30 and 40 are both connectable to the processor 5, the following operations and the like are the same. Further, even in the case of an endoscope that has an LED illumination portion at a distal end portion and that is not connected to a light source apparatus, the following operations and the like are the same.

The processor 5 has a control portion 19, a drive portion 17 that is drive means, a signal processing portion 18, a selection portion 13, and patient circuits 20 and 21. The processor 5 performs processing for displaying an image pickup signal that is picked up by either of the CCD 31 of the endoscope 30 or the CCD 41 of the endoscope 40 on the display portion 41 based on an instruction of a user that is inputted through an input portion 42 or the like.

The control portion 19 performs overall control of the processor 5, and also has a function as drive control means that controls the drive portion 17. When two endoscopes are connected, the selection portion 13 makes a selection as to which of the endoscopes to drive.

A user can connect the two endoscopes 30 and 40 to the endoscope apparatus 10. However, only one endoscope can be driven at a time. Therefore, there is a possibility that an endoscope contrary to the intention of the user will drive and the operability will be poor. That is, when a plurality of endoscopes of different kinds are connected at the same time to one endoscope apparatus, there is a risk that an endoscope of a kind that is contrary to the intention of the user will drive or will malfunction, and in some cases, it cannot be said that the operability is good. In contrast, as described later, the operability of the endoscope apparatus 10 is good because the selection portion 13 automatically selects the appropriate endoscope.

To ensure patient safety, the patient circuits 20 and 21 include isolation portions 22 and 23 for isolating a circuit portion (secondary circuit) including the display portion 41 and the like, and a circuit having the same potential as that of a circuit portion that is inserted into the body. The isolation portions 22 and 23 are described in detail later.

The selection portion 13 includes a connection detecting portion 14 that is connection detecting means, and a priority setting portion 16 that is connection priority setting means. The connection detecting portion 14 detects that an endoscope is connected to connection portion 11 or 12. When two endoscopes are connected, the priority setting portion 16 sets/stores a connection priority that determines which of the endoscopes that are connected to the connection portions is to be driven with priority by the drive portion 17, and a configuration may be adopted in which the storage contents can be changed through the input portion 42 or the like. Note that, although in FIG. 2, the selection portion 13 is arranged in the secondary circuit, at least a part thereof may be arranged in a patient circuit.

The control portion 19 controls the drive portion 17 so as to supply a drive signal to any one endoscope that the selection portion 13 selected based on the connection priority.

Note that the endoscope apparatus 10 preferably includes a notification portion that is notification means that notifies the user of the kind of endoscope that the selection portion 13 selects and the drive portion 17 is driving. For example, the notification means may display marks or the like of two kinds of endoscopes that are connected on the display portion 41, and clearly indicate the mark of the endoscope that is being driven between the two kinds of endoscopes by surrounding the mark with a frame or changing the color of the mark. Further, notification means may be provided in which LEDs are arranged in the vicinity of the connection portions 11 and 12 of the endoscope apparatus 10, so that a user can identify which of the two kinds of endoscopes is being driven based on whether an LED is lighting or based on a color of each LED. For example, a configuration may be adopted in which a state in which an LED is not lighting indicates that an endoscope is not connected, a state in which an LED lights in green indicates that an endoscope is connected, and a state in which an LED lights in red indicates a driving state.

An endoscope apparatus including notification means that notifies a user regarding which endoscope is in a driving state has better operability.

Because endoscopes that are mechanically connected to the connection portions are electrically connected to the endoscope apparatus 10, a predetermined current flows in the respective scope circuits. That is, an endoscope that is not in a driving state also consumes electric power.

To reduce power consumption, as shown in FIG. 2, the endoscope apparatus 10 includes the patient circuits 20 and 21 for the respective endoscopes, and it is preferable that the control portion 19 controls so as to supply power to only a circuit for which an operating state is required during standby also of the respective patient circuits 20 and 21. In other words, preferably the control portion 19 controls so that an endoscope and a patient circuit that are not driven consume the minimum amount of power.

Note that, there are cases where a power supply state with respect to the patient circuits 20 and 21 is switched as a result of replacement or the like of the endoscopes 30 and 40 connected to the endoscope apparatus 10. A configuration may be adopted so that, at a time of such switching of the power supply state, the control portion 19 controls the power supply state for a certain time period so as to provide a period of time in which power is not supplied to either of the patient circuits. According to the aforementioned control, the power consumption can be reduced further, a temporal margin for stopping, in a predetermined sequence, the power to the patient circuit to which power is currently being supplied can be secured, and power can be supplied to the patient circuit to which power is to be newly supplied after a signal that is outputted to the endoscope from the relevant patient circuit has entered a stable state.

Further, when switching the power supply state with respect to the patient circuits 20 and 21, preferably the control portion 19 initializes a setting for controlling a patient circuit that is held inside the control portion 19. Since the aforementioned setting that had been in effect prior to switching a patient circuit is not continued after switching the patient circuit, a system error that is caused by a mismatch between a setting that is being held in the control portion 19 and a patient circuit that is controlled by the control portion 19 after switching the power supply state can be prevented.

In addition, preferably the control portion 19 controls the signal processing portion 18 so as to stop a video signal (so as not to output a video signal to the display portion 41) for a certain time period during switching of the power supply state with respect to the patient circuits 20 and 21. This is done to ensure that a garbled video is not displayed on the display portion 41 when switching the power supply state with respect to the patient circuits.

Because the control portion 19 that is arranged in the secondary circuit has a patient circuit control function, the respective patient boards 20 and 21 are independent structures. It is therefore simple to increase or decrease the number of patient circuits connected to the secondary circuit, and development of a new patient circuit is also facilitated.

In addition, since the load of the power supply circuits of the patient boards 20 and 21 is small because the control timings of the patient boards 20 and 21 are adjusted on the secondary circuit side, power supply circuits having small capacities can be used. Further, because the control portion 19 controls based on connection detection information and selection information, the aforementioned information can also be stored as recorded information. When recorded information exists, at the time of a fault or the like, complication of maintenance work that is due to complication of the system can be reduced since the operating state of the endoscope system 1 can be easily ascertained.

According to the endoscope apparatus 10, even when two endoscopes are connected, since a priority is set (stored) that determines which of the endoscopes connected to the connection portions is to be driven with priority by the drive portion 17, an endoscope in accordance with the intention of the user is driven. Therefore, the operability of the endoscope apparatus 10 is good.

Note that, although the endoscope apparatus 10 to which the two endoscopes 30 and 40 can be connected at the same time is described above, the same advantageous effects can also be obtained in the case of an endoscope apparatus to which three or more endoscope apparatuses can be connected at the same time.

Second Embodiment

Figure 3:
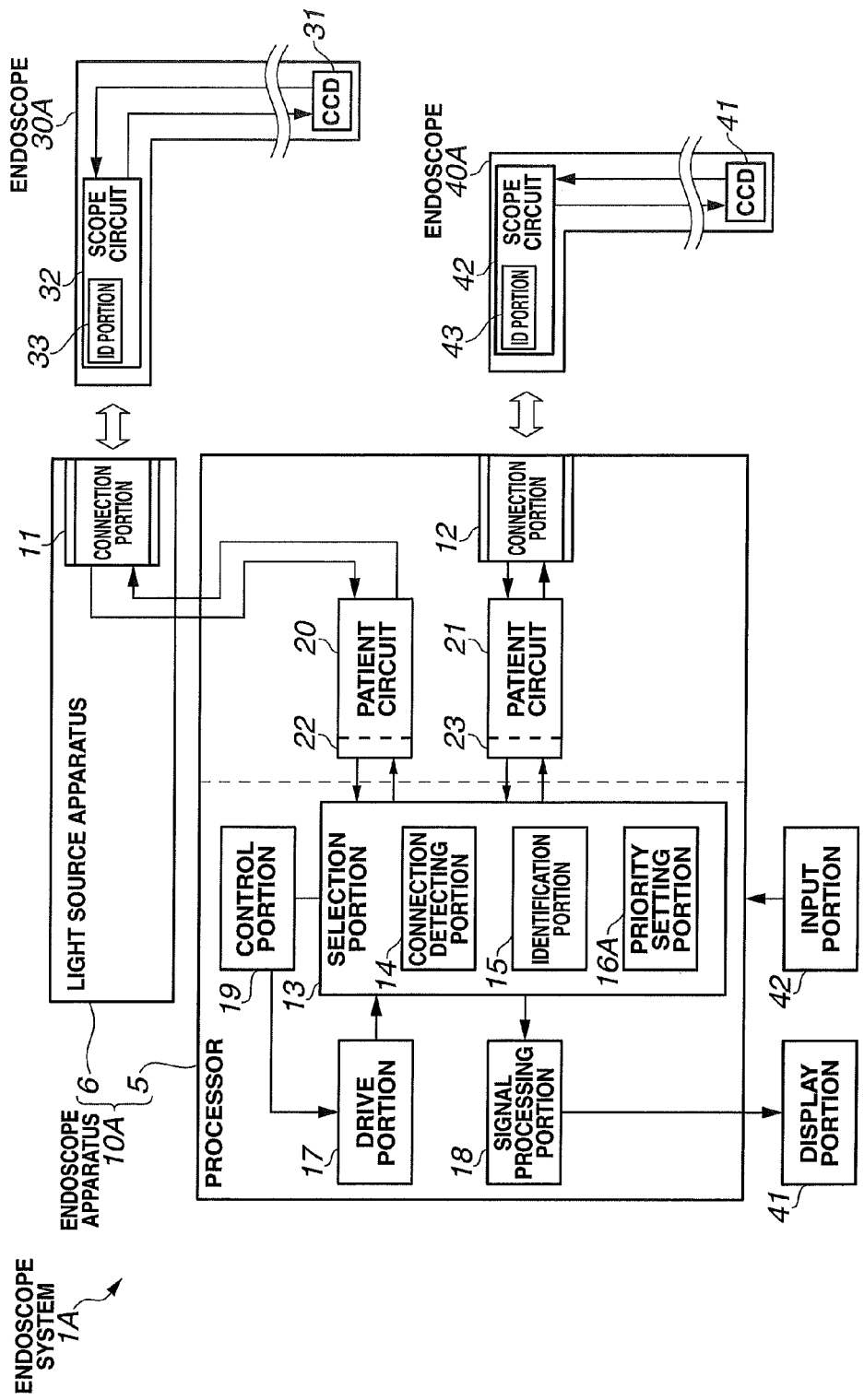
FIG. 3 is a configuration diagram of an endoscope system having an endoscope apparatus according to a second embodiment.

An endoscope apparatus 10A according to the second embodiment of the present invention that is shown in FIG. 3 is similar to the endoscope apparatus 10 according to the first embodiment, and hence the same components are denoted by the same reference symbols and a description of such components is omitted hereunder.

As shown in FIG. 3, two endoscopes 30A and 40A can be connected at the same time to an endoscope system 1A having the endoscope apparatus 10A of the present embodiment. The endoscopes 30A and 40A have ID portions 33 and 43, respectively, for identifying the kind of the endoscope.

On the other hand, a selection portion 13A of the endoscope apparatus 10A includes an identification portion 15 that is identification means and a priority setting portion 16A that is priority setting means. The identification portion 15 identifies the kind of an endoscope that is connected. The priority setting portion 16A sets and stores a kind priority that is a drive priority for each kind of endoscope. That is, the priority setting portion 16A stores information regarding which kind of endoscope the drive portion 17 is to drive with priority in a case where two endoscopes are connected, and a configuration may also be adopted in which the storage contents can be changed through the input portion 42 or the like.

In this case, the identification portion 15 identifies the kinds of the endoscopes based on, for example, a resistance value R2 of a specific resistance 33R (see FIG. 5) arranged in the ID portions 33 and 43 of the endoscopes 30 and 40. That is, specific resistances that have respectively different resistance values are arranged in the ID portions 33 and 34 of the endoscopes that are of different kinds. The relationship between the kinds of endoscopes and the resistance values of the specific resistances is previously determined.

According to the endoscope apparatus 10A, even when two endoscopes are connected at the same time, because the identification portion 15 identifies the kinds of the endoscopes, and a priority that determines which kind of endoscope is to be driven with priority by the drive portion 17 is set and stored by the priority setting portion 16A, the endoscope of the kind that matches the intention of the user is automatically driven. Therefore, the operability of the endoscope apparatus 10A is good.

Figure 4:
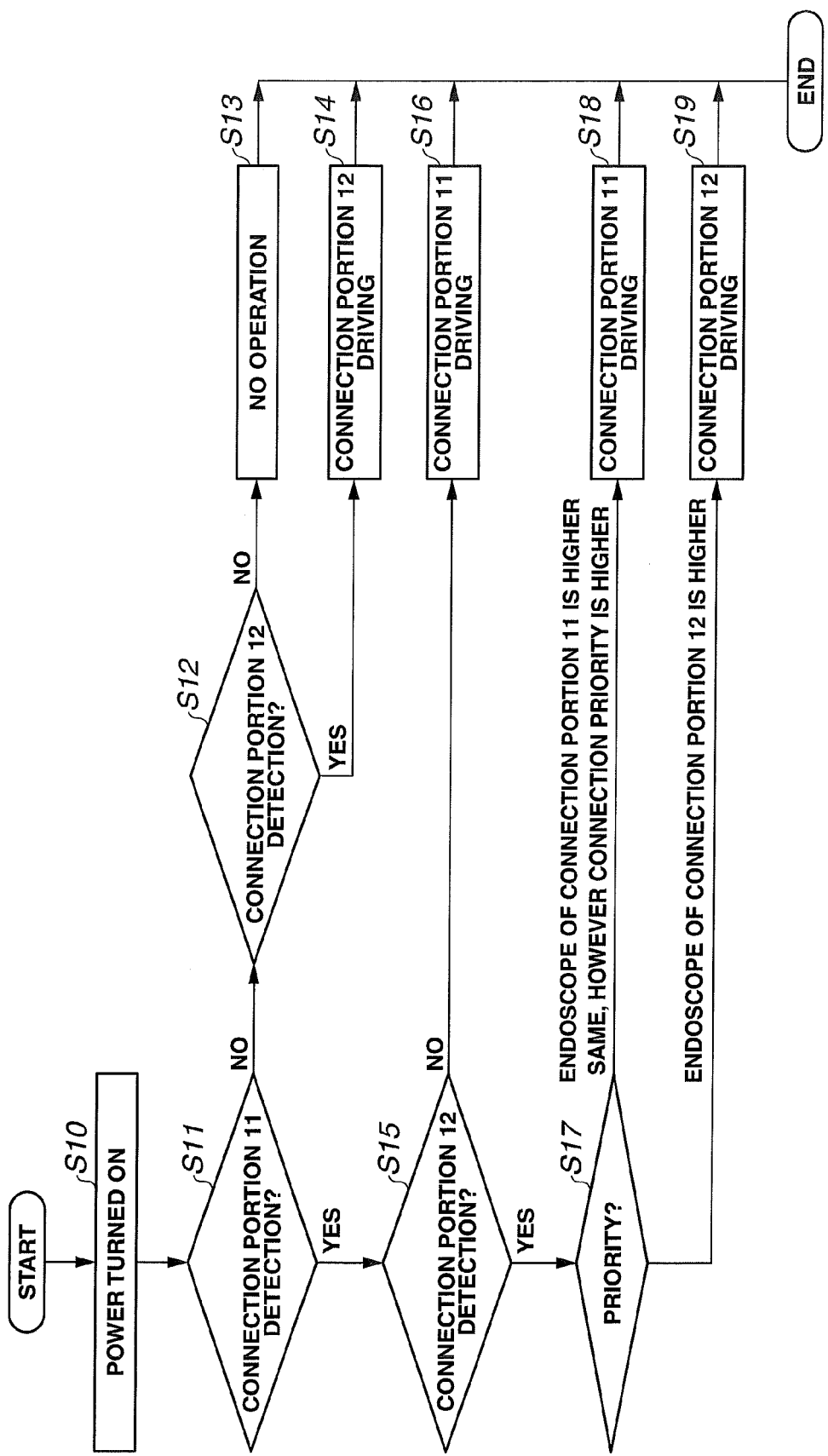
FIG. 4 is a flowchart for describing the flow of operations of the endoscope apparatus of the second embodiment.

Note that, in the endoscope apparatus 10A, the priority setting portion 16A may store not only a kind priority that is a drive priority for each kind of endoscope, but may also store a connection priority that is the priority of the connection portions, similarly to the priority setting portion 16 of the first embodiment. Hereunder, the flow of processing of a control method for the endoscope apparatus is described using the flowchart shown in FIG. 4.

<Step S10> Power on

The power of the endoscope apparatus is turned on.

<Step S11> Connection Portion 11 Detection

The connection detecting portion 14 detects whether or not an endoscope is connected to the connection portion 11.

<Step S12> Connection Portion 12 Detection

If an endoscope is not connected to the connection portion 11 (S11: No), the connection detecting portion 14 detects whether or not an endoscope is connected to the connection portion 12.

<Step S13> No Operation

If an endoscope is not connected to the connection portion 11 and the connection portion 12 (S12: No), the drive portion 17 does not operate.

<Step S14> Connection Portion 12 Driving

If an endoscope is connected to the connection portion 12 (S12: Yes), the drive portion 17 drives the endoscope that is connected to the connection portion 12.

<Step S15> Connection Portion 12 Detection

If an endoscope is connected to the connection portion 11 (S11: Yes), the connection detecting portion 14 detects whether or not an endoscope is connected to the connection portion 12.

<Step S16> Connection Portion 11 Driving

If an endoscope is not connected to the connection portion 12 (S15: No), the drive portion 17 drives the endoscope that is connected to the connection portion 11.

<Step S17> Order of Priority Determination

If endoscopes are connected to the connection portion 11 and the connection portion 12 (S15: Yes), the selection portion 13 selects the endoscope to drive in accordance with the setting of the priority setting portion 16A based on the endoscope kinds identified by the identification portion 15 and the connection portions.

<Step S18> Connection Portion 11 Driving

If the priority of the endoscope connected to the connection portion 11 is higher than the priority of the endoscope connected to the connection portion 12, or if the kind priority is the same for the two endoscopes and the connection priority of the connection portion 11 is higher, the drive portion 17 drives the endoscope connected to the connection portion 11.

<Step S19> Connection Portion 12 Driving

If the priority of the endoscope connected to the connection portion 12 is higher than the priority of the endoscope connected to the connection portion 11, or if the kind priority is the same for the two endoscopes and the connection priority of the connection portion 12 is higher, the drive portion 17 drives the endoscope connected to the connection portion 12.

Note that, when an endoscope has been replaced, the processing from step S11 is performed again.

When two endoscopes for which the kind priority is the same are connected at the same time, on the basis of the connection priority, the above described endoscope apparatus can select an endoscope to which the drive portion 17 is to supply a drive signal. Therefore, this endoscope apparatus has even better operability.

<Modification of Second Embodiment>

Figure 5:
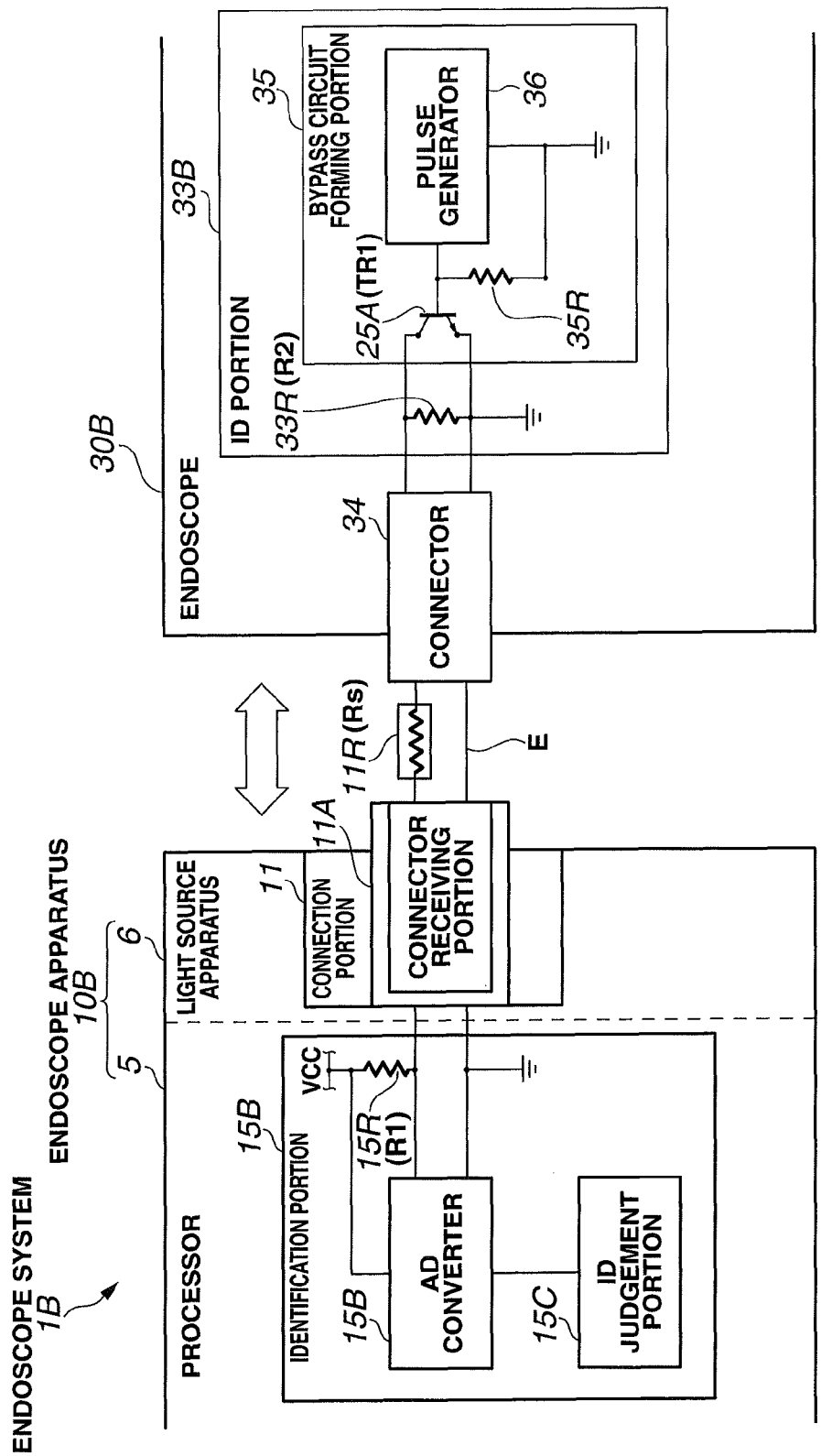
FIG. 5 is a configuration diagram of an endoscope system having an endoscope apparatus according to a modification of the second embodiment.

FIG. 5 is a partial circuit diagram of an endoscope system 1B that includes an endoscope apparatus 10B according to a modification of the second embodiment and an endoscope 30B. The endoscope apparatus 10B according to the present modification is similar to the endoscope apparatus 10A, and hence the same components are denoted by the same reference symbols and a description of such components is omitted hereunder.

As shown in FIG. 5, in the endoscope apparatus 10A, for example, an identification portion 15B identifies the kind of the endoscope 30B based on a resistance value R2 of the specific resistance 33R that is arranged in an ID portion 33B of the endoscope 30B. However, due to a contact resistance 11R that arises in the connection portion 11, there is a possibility that the identification portion 15B cannot detect the correct resistance value R2 of the specific resistance 33R.

In the endoscope system 1B, when a connector 34 of the endoscope 30B is connected to a connector receiving portion 11A of the connection portion 11 of the endoscope apparatus 10B, a large number of signal lines are connected through a large number of electric contacts. Among the large number of signal lines, only an ID signal line for identifying the endoscope kind and a ground potential line E are shown in FIG. 5.

A contact resistance 11R arises at an electric contact of the ID signal line between the connector receiving portion 11A of the connection portion 11 of the endoscope apparatus 10B and the connector 34 of the endoscope 30B. Note that, with regard to a contact resistance of an electric contact of the ground potential line E, since there are in fact not one but a plurality of connection contacts in the ground potential line E, the contact resistance can be ignored since the contact resistance is extremely small compared to the contact resistance 11R of the electric contact of the ID signal line.

As shown in FIG. 5, the endoscope 30B includes: the ID signal line and ground line E that are connected to the endoscope apparatus 10B through the connection portion 11; the specific resistance 33R that electrically connects the ID signal line and the ground line E; and a bypass circuit forming portion 35 that is capable of forming a bypass circuit that short-circuits the specific resistance 33R. The bypass circuit forming portion 35 includes a pulse generator 36, a pull-down resistance 35R, and a voltage change transistor 35A. When the pulse generator 36 generates a pulse voltage signal, since the voltage change transistor 35A enters an "on" state by means of the pull-down resistance 35R and a bypass circuit is formed, a state (short-circuit state) is entered in which both ends of the specific resistance 33R are connected.

The identification portion 15 of the endoscope apparatus 10B includes a reference resistance 15R of a predetermined resistance value R1, a voltage application portion (not shown) that applies a predetermined voltage VCC, an AD converter 15B, and an ID judgement portion 15C. The AD converter 15B converts an inputted voltage signal into a digital signal, and the ID judgement portion identifies the kind of endoscope based on the digital signal received from the AD converter 15B.

Figure 6A:
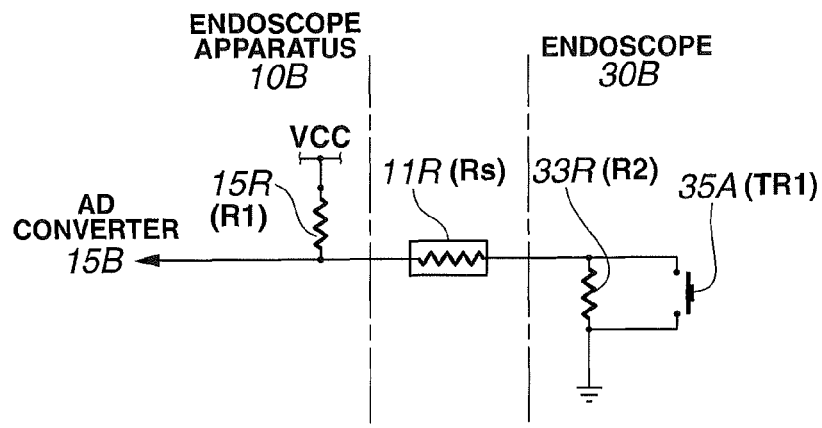
FIG. 6A is a circuit diagram for describing operations of a recognition portion of the endoscope apparatus according to the modification of the second embodiment.
Figure 6B:
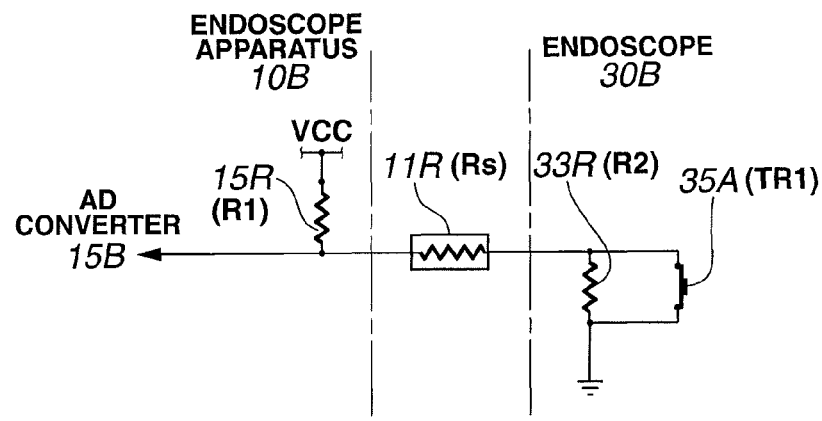
FIG. 6B is a circuit diagram for describing operations of the recognition portion of the endoscope apparatus according to the modification of the second embodiment.

Next, a method for cancelling the contact resistance 11R in an operation to identify the kind of an endoscope is described using FIG. 6A to FIG. 6C. As shown in FIG. 6A, when the voltage change transistor 35A of the endoscope 30B is in an "off" state, a voltage V1 that is inputted to the AD converter 15B is a value calculated by equation 1 below.

$$V1 = VCC \times (Rs+R2)/(R1+Rs+R2) \quad \text{(equation 1)}$$

Here, when a contact resistance Rs is small (Rs≈0), a voltage V2 is a value calculated by equation 2 below.

$$V2 = VCC \times (R2)/(R1+R2) \quad \text{(equation 2)}$$

Since the resistance value R1 of the reference resistance 15R and VCC are known, the ID judgement portion 15C can calculate the resistance value of the specific resistance 33R of the connected endoscope based on a partial voltage of the reference resistance 15R. Therefore, the identification portion 15 identifies the endoscope kind based on correlations between resistance values of specific resistances and endoscope kinds that are stored in the priority setting portion 15A.

However, when the contact resistance Rs is large, a resistance value of the specific resistance 33R calculated based on equation 2 may be an erroneous value. In such case, the identification portion 15B mistakes the kind of endoscope that is connected.

A case in which, for instance, the resistance value R1 of the reference resistance 15R and the resistance value R2 of the specific resistance 33R are the same, and the resistance value Rs of the contact resistance 11R is a multiple of 10 relative to the resistance value R1 of the reference resistance 15R will now be described as an example.

A voltage V3 in this case is a value calculated by equation 3 below.

$$V3 = VCC \times (10 \times R1+R2)/(R1+10 \times R1+R2) \quad \text{(equation 3)}$$

In this case, the identification portion 15B determines that the resistance value of the specific resistance 33R is a multiple of 11 relative to the resistance value of the reference resistance 15R, and as a result, erroneously identifies the kind of the endoscope.

However, in the endoscope apparatus 10B, the resistance value R2 of the specific resistance 33R can be detected by cancelling the contact resistance Rs in the connection portion 11 by detecting the contact resistance Rs of the ID signal line that connects the endoscope 30B and the endoscope apparatus, based on a partial voltage of the reference resistance 15R when a bypass circuit is formed by the bypass circuit forming portion 35.

That is, as shown in FIG. 6B, when the voltage change transistor 35A of the endoscope 30B is in an "on" state, a voltage V4 that is inputted to the AD converter 15B is a value calculated by equation 4 below.

$$V4 = VCC \times (Rs)/(R1+Rs) \quad \text{(equation 4)}$$

That is, the ID judgement portion 15C can calculate the resistance value Rs of the contact resistance 11R in the connection portion 11 based on equation 4.

Thus, the identification portion 15B can accurately identify the kind of the endoscope based on the resistance value R2 of the specific resistance 33R that is calculated by cancelling the contact resistance Rs in the connection portion 11 from equation 1 based on the calculated resistance value Rs.

As described above, in addition to the advantageous effects of the endoscope apparatus 10A of the second embodiment, the endoscope apparatus 10B of the present modification can identify the kind of a connected endoscope more accurately and thus the endoscope apparatus 10B has better operability.

Third Embodiment

An endoscope apparatus 10C according to a third embodiment of the present invention that is shown in FIG. 2 is similar to the endoscope apparatus 10 according to the first embodiment and the like, and hence the same components are denoted by the same reference symbols and a description of such components is omitted hereunder.

As described in the foregoing, to ensure safety, in the endoscope apparatus 10C, circuits (patient circuits) through which a current flows that is of the same level as a current that flows through the inside of a member that is inserted into the body of a patient, and a circuit (secondary circuit) that is connected to peripheral equipment such as a monitor are isolated by isolation portions 22 and 23. Further, a current that flows through the patient circuits is a low current that exerts little influence on a patient.

Figure 7:
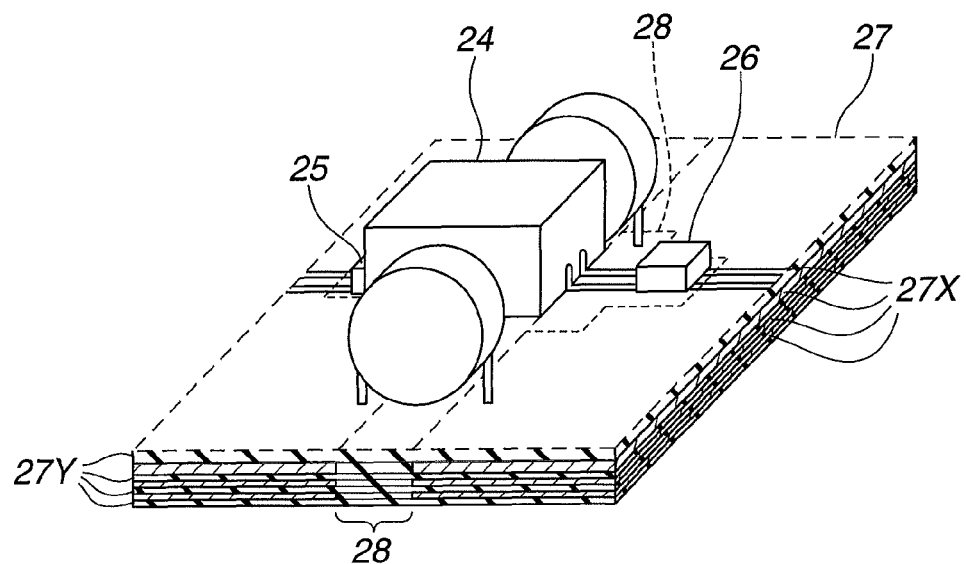
FIG. 7 is a perspective view of an isolation portion of an endoscope apparatus according to a third embodiment.

For example, as shown in FIG. 7, the isolation portion 22 includes a pulse transformer 24, and two common mode noise filters (common mode chokes) 25 and 26 that are connected to a primary side and a secondary side of the pulse transformer 24. The pulse transformer 24 and the common mode noise filters 25 and 26 are surface-mounted onto a multilayer wiring board 27. Note that, with regard to the common mode noise filters 25 and 26, it is preferable that a differential impedance with respect to a signal frequency and a triple frequency be high.

Figure 8:
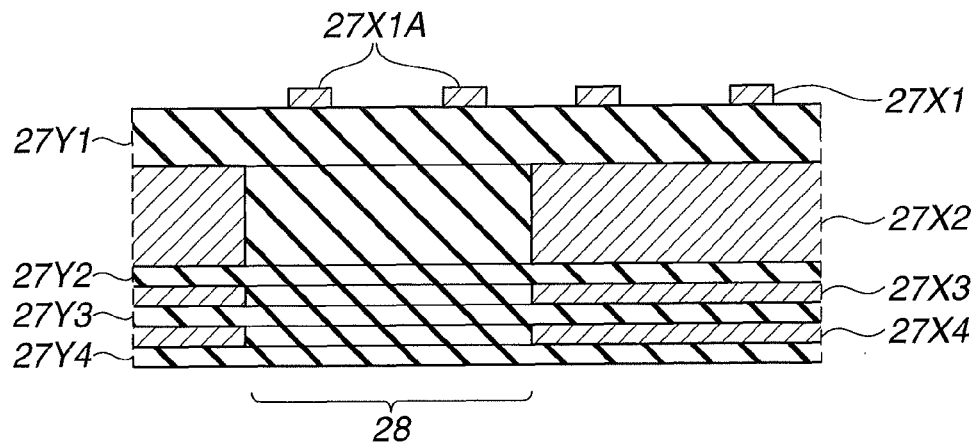
FIG. 8 is a view for describing a cross-sectional structure of a multilayer wiring board of the isolation portion of the endoscope apparatus according to the third embodiment.

As shown in FIG. 7 and FIG. 8, a plurality of conductor layers 27X (27X1 to 27X4) that are insulated with dielectric layers (insulating layers) 27Y (27Y1 to 27Y4) are laminated in the multilayer wiring board 27, and the patterned conductor layers 27X form an electric circuit through conductive wiring of the dielectric layers 27Y. The conductor layer 27X1 that is the uppermost layer is wiring that connects the pulse transformer 24 and the common mode noise filters 25 and 26. The conductor layer 27X2 is a ground potential layer (GND layer). Wiring constituted by the conductor layer 27X1 that is the uppermost layer and the conductor layer 27X2 are designed so as to enter a predetermined coupled state for performing efficient high-frequency transmission, for example, a state in which a characteristic impedance is 50Ω.

In the multilayer wiring board 27, there are no conductor layers 27X in a region 28 below and around the pulse transformer 24 and the common mode noise filters 25 and 26. That is, the conductor layers 27X in the region 28 of the multilayer wiring board 27 are removed by patterning.

This is done to prevent the occurrence of radiation noise (radiation of a high-frequency signal component) caused by transmission of a high-frequency differential signal through the pulse transformer 24. Although use of a low-pass filter or the like is also possible to reduce radiation noise, the transmission characteristics deteriorate when transmitting a high frequency signal.

However, by removing the conductor layers 27X in the region 28, it is possible to prevent common mode noise that is generated at a coil from coupling with the conductor layers 27X2 to 27X4, and particularly, the conductor layer 27X2 that is the GND layer.

That is, to prevent common mode noise generated at a primary side coil from returning to a transmission signal line, the common mode noise filter 26 is arranged, and furthermore, conductor layers below the pulse transformer 24 that includes a common mode component and the common mode noise filter 26 are removed.

Further, to prevent common mode noise generated at a secondary side coil from going towards a reception signal line, the common mode noise filter 25 is arranged, and furthermore, conductor layers below the pulse transformer 24 that includes a common mode component and the common mode noise filter 25 are removed.

Therefore, a signal line 27X1A that transmits a signal that includes common mode noise does not couple with the conductor layer 27X2 and the like.

For example, by removing the conductor layers 27X of the region 28, when transmitting a differential signal having a frequency of 204 MHz, a radiation noise component of 816 MHz that is a multiple of three relative thereto can be reduced to 7 dB.

Note that, although the region 28 is at least a region that is directly below the pulse transformer 24 and the common mode noise filters 25 and 26, that is, a region inside the component mounting area, preferably the region 28 includes a peripheral region of the region directly below the aforementioned components. Here, the term "peripheral region" refers to, for example, a region within a range of 100% to 150% relative to the component mounting area, and for example, is within a range of 0 mm to 20 mm from directly below the component mounting area to outside. If the "peripheral region" is within the above-described range, occurrence of radiation noise can be efficiently suppressed without the wiring board getting larger.

Figure 9A:
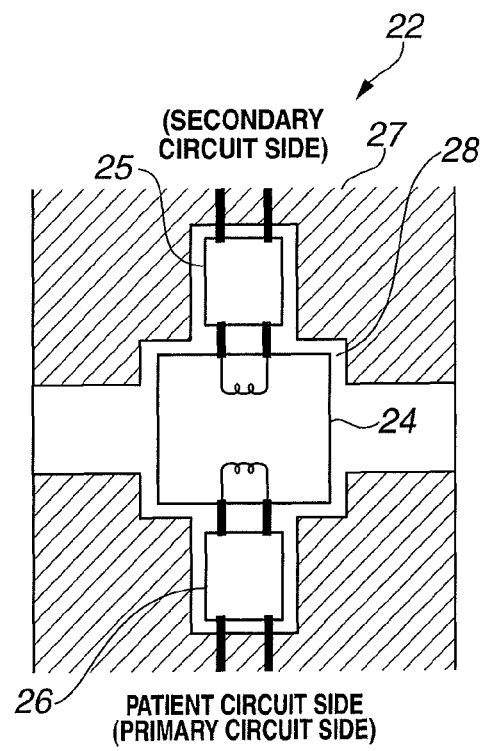
FIG. 9A is a view for describing the structure of the multilayer wiring board of the isolation portion of the endoscope apparatus according to the third embodiment.

That is, as shown in FIG. 9A, the region 28 from which the conductor layers 27X are removed is below and around the pulse transformer 24 and the common mode noise filters 25 and 26. Note that, because the conductor layers 27X between the primary circuit and secondary circuit are insulated, the ground potential layer (GND layer) 27X2 is also removed.

Figure 9B:
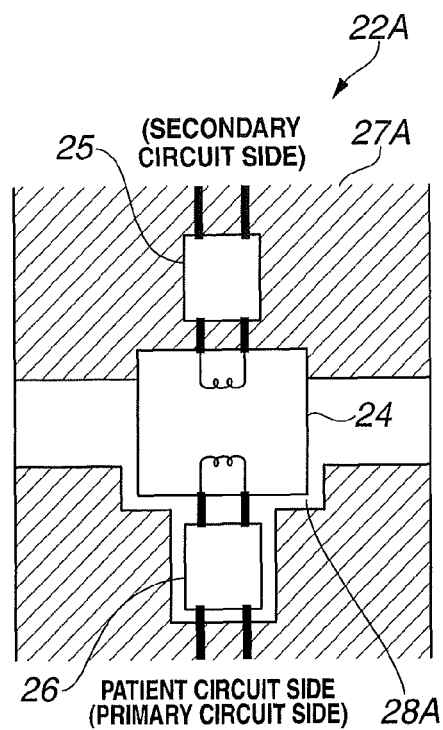
FIG. 9B is a view for describing the structure of the multilayer wiring board of the isolation portion of the endoscope apparatus according to the third embodiment.

Note that, as shown in FIG. 9B, a radiation noise reducing effect is also obtained in the case of a wiring board 27A in which conductor layers 27X are removed from a region 28A below and around the pulse transformer 24 and the common mode noise filter 25.

Figure 9C:
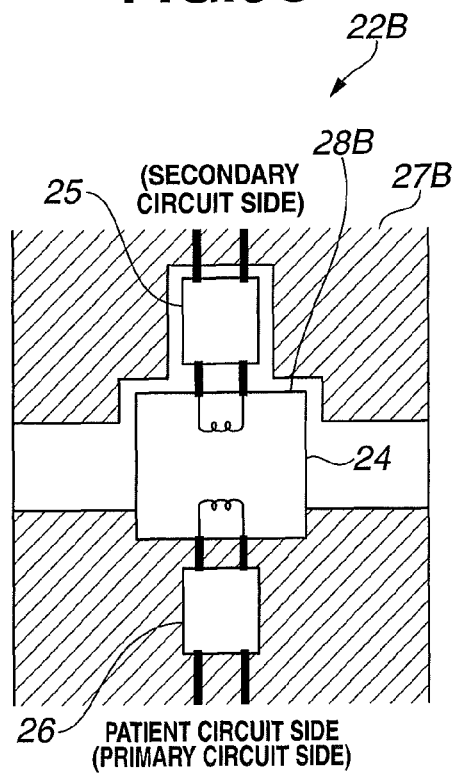
FIG. 9C is a view for describing the structure of the multilayer wiring board of the isolation portion of the endoscope apparatus according to the third embodiment.

Similarly, as shown in FIG. 9C, a radiation noise reducing effect is also obtained in the case of a wiring board 27B in which conductor layers 27X are removed from a region 28B below and around the pulse transformer 24 and the common mode noise filter 26.

As described above, the endoscope apparatus 10C has the advantageous effects of the endoscope apparatus 10 and the like, and can also reduce radiation noise.

Fourth Embodiment

Figure 10:
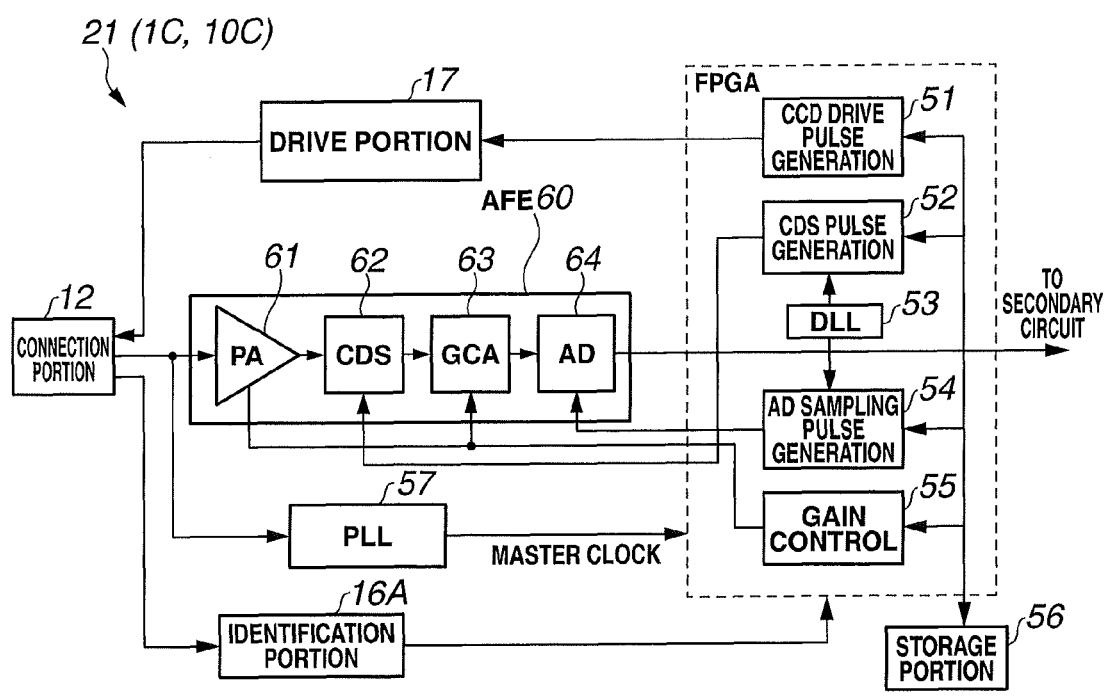
FIG. 10 is a configuration diagram for describing a signal processing portion of an endoscope apparatus according to a fourth embodiment.

An endoscope apparatus 10C of an endoscope system 1C according to the fourth embodiment of the present invention that is shown in FIG. 10 is similar to the endoscope apparatus 10A according to the second embodiment and the like, and hence the same components are denoted by the same reference symbols and a description of such components is omitted hereunder.

In the analog signal processing circuit of the patient circuit 21 of the endoscope apparatus 10A in which different kinds of analog endoscopes, for example, each of three kinds of endoscopes can be connected to the connection portions 12, signal processing circuits of a plurality of systems that correspond to the respective endoscopes are required.

In contrast, as shown in FIG. 10, an analog signal processing circuit 21C including an AFE (analog front end) portion 60 of the endoscope apparatus 10C is a common circuit that performs processing for endoscopes of different kinds.

The endoscope apparatus 10C has a storage portion 56 that stores AFE gain settings and setting values for CDS/ADC sampling timing and the like according to the kinds of endoscopes.

When an endoscope is connected, the kind of endoscope that is connected is identified by the identification portion 15 that is a scope detection circuit.

The AFE portion 60 includes a PA (preamplification) portion 61, a CDS (correlation double sampling) portion 62, a GCA portion 63 that is an analog gain control amplifier, and an AD conversion portion 64.

A signal that drives a CCD of an endoscope, a CDS/AD sampling pulse, and an AFE gain are generated by a digital circuit that includes an FPGA (field programmable gate array) 50 based on a scope detection signal from the scope detection circuit. That is, the FPGA 50 includes a CCD drive pulse generation portion 51, a CDS pulse generation portion 52, an AD sampling pulse generation portion 54, a gain control portion 55, and a DLL (phase delay) circuit 53.

The CDS/AD sampling pulse is outputted after the pulse width and phase thereof is adjusted by a PLL (frequency multiplier) circuit 57 and the DLL circuit 53 based on a clock signal regenerated by an output signal from the CCD. Further, a digital video signal is transmitted to the secondary circuit on the basis of a phase of the clock signal regenerated by a CCD output signal. In addition, a phase difference between the clock signal regenerated by the CCD output signal and a clock signal (master clock signal) from the secondary side is detected by the FPGA 50, and processing is performed so that a pixel deviation or the like does not occur.

In addition to the advantageous effects of the endoscope apparatus 10A, according to the endoscope apparatus 10C, a decrease in the number of components, a cost reduction, and a decrease in the wiring board area are achieved. Further, since various pulse signals used for processing are managed by the same FPGA 50, a problem such as a pixel deviation does not arise.

Note that, although the analog signal processing circuit 21C is arranged in a patient circuit of the endoscope apparatus in the case of an analog endoscope, the analog signal processing circuit 21C may be arranged in an endoscope. For example, in the endoscope 30 that is a digital endoscope that is described in the first embodiment, the AFE circuit 60 and the like are arranged in the scope circuit 32.

The present invention is not limited to the above-described embodiments and modification and the like, and various changes and alterations can be made within a range that does not depart from the spirit and scope of the present invention.

What is claimed is:

1. An endoscope apparatus, comprising:
   a plurality of connection portions to which an endoscope can be connected, respectively;
   a priority setting portion that, when a plurality of endoscopes are connected to the plurality of connection portions, sets a drive priority for selecting one endoscope to supply a drive signal to, wherein the drive priority is a kind priority that corresponds to a kind of the endoscope;
   a drive portion that supplies a drive signal to one endoscope; and
   a drive control portion that controls so that the drive portion supplies the drive signal only to any one endoscope based on the drive priority;
   an identification portion that identifies the kind based on a resistance value of a specific resistance that differs according to a kind of the endoscope that is arranged in the endoscope, and that is detected by cancelling a contact resistance in the connection portion, wherein the identification portion comprises;
   an ID signal line and a ground line to which the endoscope is connected through the connection portion, wherein the specific resistance electrically connects the ID signal line and the ground line;
   a bypass circuit forming portion capable of forming a bypass circuit that short-circuits the specific resistance; and
   a reference resistance of a predetermined resistance value, wherein a predetermined voltage is applied to the reference resistance and the specific resistance that are serially connected through the ID signal line, and detects a resistance value of the specific resistance based on a partial voltage of the reference resistance, and also detects a resistance value of the specific resistance by cancelling the contact resistance by detecting a contact resistance in the connection portion of the ID signal line based on a partial voltage of the reference resistance when the bypass circuit is formed.

2. The endoscope apparatus according to claim 1, wherein the drive priority is a connection priority corresponding to the plurality of connection portions.

3. The endoscope apparatus according to claim 1, wherein:
   the drive priority is a connection priority corresponding to the plurality of connection portions, and a kind priority corresponding to kinds of the endoscopes; and
   when a plurality of endoscopes for which the kind priority is identical are connected, the drive control portion selects an endoscope that the drive portion supplies the drive signal to, based on the connection priority.

4. The endoscope apparatus according to claim 1, comprising a multilayer wiring board on which a pulse transformer that is an isolation portion for isolating a patient circuit, and two common mode noise filters that are connected to a primary side and a secondary side of the pulse transformer, respectively, are mounted, wherein there is no conductor layer directly below a mounting location of the pulse transformer and the two common mode noise filters of the multilayer wiring board.

* * * * *